United States Patent
Dugstad et al.

(10) Patent No.: US 6,217,850 B1
(45) Date of Patent: Apr. 17, 2001

(54) METHOD OF MAKING LYOPHILIZED MICROBUBBLE COMPOSITIONS USEFUL AS CONTRAST AGENTS

(75) Inventors: Harald Dugstad; Jo Klaveness; Pål Rongved; Roald Skurtveit; Jorunn Braenden, all of Oslo (NO)

(73) Assignee: Nycomed Imaging AS, Oslo (NO)

(*) Notice: Subject to any disclaimer, the term of this patent is extended or adjusted under 35 U.S.C. 154(b) by 0 days.

(21) Appl. No.: 09/084,105

(22) Filed: May 26, 1998

Related U.S. Application Data (63) Continuation of application No. 08/776,647, filed as application No. PCT/GB96/01361 on Feb. 7, 1997, now abandoned.

(30) Foreign Application Priority Data

Jun. 7, 1995 (GB) .................................................. 9511488
Feb. 19, 1996 (GB) .................................................. 9603466

(51) Int. Cl.$^7$ .............................. A61B 8/00; B01J 13/02; B32B 15/02; B01F 17/00
(52) U.S. Cl. ................ 424/9.52; 427/213.3; 427/213.31; 428/402; 516/10
(58) Field of Search ................ 424/9.52, 9.51, 424/9.5, 450, 489; 600/441, 458; 428/402, 402.2; 516/10, 12, 77; 427/212, 213.3, 213.31

(56) References Cited

U.S. PATENT DOCUMENTS

| | | | |
|---|---|---|---|
| 4,544,545 | * 10/1985 | Ryan et al. ......................... | 424/1.11 |
| 5,228,446 | * 7/1993 | Unger et al. ..................... | 128/662.02 |
| 5,445,813 | * 8/1995 | Schneider et al. .................. | 424/9.51 |
| 5,498,421 | * 3/1996 | Grinstaff et al. ..................... | 424/450 |
| 5,542,935 | * 8/1996 | Unger et al. ......................... | 604/190 |
| 5,599,523 | * 2/1997 | Beller et al. ......................... | 424/9.52 |
| 5,811,118 | * 9/1998 | Ostro et al. ......................... | 424/450 |
| 5,830,430 | * 11/1998 | Unger et al. ....................... | 424/1.21 |

FOREIGN PATENT DOCUMENTS

| | | |
|---|---|---|
| 0 494 615 | 7/1992 | (EP) . |
| 91 15244 | 10/1991 | (WO) . |
| 94 09829 | 5/1994 | (WO) . |
| 95 05854 | 3/1995 | (WO) . |

OTHER PUBLICATIONS

Schneider et al., *Investigative Radiology*, vol. 30, No. 8, Aug. 1995, 451–457.
Richardson et al., *Journal of Nuclear Medicine*, vol. 19, No. 9, Sep. 1978, 1049–1054.
Hnatowich et al., *Journal of Nuclear Medicine*, vol. 21, No. 7, Jul. 1980, 662–669.

* cited by examiner

Primary Examiner—Michael G. Hartley
(74) Attorney, Agent, or Firm—Bacon & Thomas (57) ABSTRACT

Microbubble dispersions stabilised by phospholipids predominantly comprising molecules which individually have an overall net charge exhibit advantageous stability, rendering them useful both as efficacious contrast agents per se and as intermediates in the preparation of contrast agents wherein the phospholipids are crosslinked or polymerised. An improved process for preparing microbubble-containing contrast agents is also disclosed, this comprising lyophilising an aqueous dispersion of gas microbubbles stabilised by one or more membrane-forming lipids to yield a dried product which may be reconstituted in an injectable carrier liquid to generate a microbubble-containing contrast agent.

12 Claims, 1 Drawing Sheet

FIG. 1.1

METHOD OF MAKING LYOPHILIZED MICROBUBBLE COMPOSITIONS USEFUL AS CONTRAST AGENTS

This application is a continuation of application Ser. No. 08/776,647, filed Feb. 7, 1997, now abandoned, which is a 371 application of PCT/GB96/01361 filed Jun. 7, 1996.

This invention relates to novel gas-containing contrast agents of use in diagnostic imaging, more particularly to such contrast agents comprising phospholipid-stabilised gas microbubbles and to a novel method for the preparation of gas-containing contrast agents.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents or intravascular contrast agents.

The use of radioactive gases, e.g. radioactive isotopes of inert gases such as xenon, has also been proposed in scintigraphy, for example for blood pool imaging.

Initial studies involving free gas bubbles generated in vivo by intracardiac injection of physiologically acceptable substances have demonstrated the potential efficiency of such bubbles as contrast agents in echography; such techniques are severely limited in practice, however, by the short lifetime of the free bubbles. Interest has accordingly been shown in methods of stabilising gas bubbles for echocardiography and other ultrasonic studies, for example using emulsifiers, oils;, thickeners or sugars, or by entraining or encapsulating the gas or a precursor therefor in a variety of systems, e.g. as porous gas-containing microparticles or as encapsulated gas microbubbles.

There is a body of prior art regarding use of phospholipids as components of gas-containing ultrasound contrast agents. Thus, for example, the use as ultrasound contrast media of phospholipid liposomes in which a lipid bilayer surrounds a confined composition including a gas or gas precursor is disclosed in U.S. Pat. No. 4,900,540. The encapsulated material is typically a gas precursor such as aqueous sodium bicarbonate, which is said to generate carbon dioxide following administration through exposure to body pH. The cores of the resulting liposomes will therefore tend to comprise liquid containing extremely small microbubbles of gas which will exhibit only limited echogenicity by virtue of their small size.

WO-A-9115244 discloses ultrasound contrast media comprising microbubbles of air or other gas formed in a suspension of liquid-filled liposomes, the liposomes apparently stabilising the microbubbles. Such systems are differentiated from those of the above-mentioned U.S. Pat. No. 4,900,540 in which the air or other gas is inside the liposomes.

WO-A-9211873 describes aqueous preparations designed to absorb and stabilise microbubbles and thereby serve as ultrasound contrast agents, the compositions comprising polyoxyethylene/polyoxypropylene polymers and negatively charged phospholipids. The weight ratio of polymer to phospholipid is typically about 3:1.

Ultrasound contrast agents comprising gas-filled liposomes, i.e. liposomes which are substantially devoid of liquid in the interior thereof, and their preparation by a vacuum drying gas instillation method are described in WO-A-9222247. The preparation of such gas-filled liposomes by a gel state shaking gas instillation method is described in WO-A-9428780. A report on gas-filled lipid bilayers composed of dipalmitoylphosphatidylcholine as ultrasound contrast agents is presented by Unger et al. in Investigative Radiology 29, Supplement 2, S134–S136 (1994).

WO-A-9409829 discloses injectable suspensions of gas microbubbles in an aqueous carrier liquid comprising at least one phospholipid stabiliser, the concentration of phospholipids in the carrier being less than 0.01% w/w but equal to or above the amount at which phospholipid molecules are present solely at the gas microbubble-liquid interface. The amount of phospholipid may therefore be as low as that necessary for formation of a single monolayer of surfactant around the gas microbubbles, the resulting film-like structure stabilising the bubbles against collapse or coalescence. Microbubbles with a liposome-like surfactant bilayer are said not to be obtained when such low phospholipid concentrations are used.

A further body of prior art concerns selection of gases for gas microbubble-containing ultrasound contrast media in order to enhance properties such as their stability and duration of echogenic effect. Thus, for example, WO-A-9305819 proposes use of free microbubbles of gases having a coefficient Q greater than 5 where $$Q=4.0 \times 10^{-7} \times \rho / C_s D$$

(where $\rho$ is the density of the gas in kg.m$^{-3}$, $C_s$ is the water solubility of the gas in moles.l$^{-1}$ and D is the diffusivity of the gas in solution in cm$^3$.sec-$^{-1}$). An extensive list of gases said to fulfil this requirement is presented.

EP-A-0554213 suggests that one may impart resistance against collapse under pressure to gas-filled microvesicles by introduction thereto of at least one gas whose solubility in water, expressed in litres of gas/litres of water under standard conditions, divided by the square root of its molecular weight does not exceed 0.003. Preferred gases are said to include sulphur hexafluoride, selenium hexafluoride and various Freons®. Such gases may, inter alia, be used in phospholipid-containing compositions of the type described in the above-mentioned WO-A-9215244.

Schneider et al. in Investigative Radiology 30(8), pp.451–457 (1995) describe a new ultrasonographic contrast agent based on sulphur hexafluoride-filled microbubbles apparently stabilised by a combination of polyethyleneglycol 4000 and a mixture of the phospholipids distearoylphosphatidylcholine and dipalmitoylphosphatidylglycerol. The use of sulphur hexafluoride rather than air is said to provide improved resistance to pressure increases such as occur in the left heart during systole.

WO-A-9503835 proposes use of mlcrobubbles containing a gas mixture the composition of which is based on considerations of gas partial pressures both inside and outside the microbubbles, so as to take account of osmotic effects on microbubble size. Representative mixtures comprise a gas having a low vapour pressure and limited solubility in blood or serum (e.g. a fluorocarbon) in combination with another gas which is more rapidly exchanged with gases present in normal blood or serum (e.g. nitrogen, oxygen, carbon dioxide or mixtures thereof).

WO-A-9516467 suggests use of ultrasound contrast media containing a mixture of gases A and B, where gas B is present in an amount of 0.5–41% v/v, has a molecular weight greater than 80 daltons and has aqueous solubility below 0.0283 ml/ml water under standard conditions, the balance of the mixture being gas A. Representative gases A include air, oxygen, nitrogen, carbon dioxide and mixtures thereof. Representative gases B include fluorine-containing gases such as sulphur hexafluoride and various perfluorinated hydrocarbons. Preferred stabilisers in such contrast media include phospholipids.

Phospholipids said to be useful in prior art contrast agents include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; mixtures of any of the foregoing and mixtures with other lipids such as cholesterol. Lecithin derivatives generally appear to be the most commonly used phospholipids, possibly by virtue of their ready availability from natural sources. The use of additives such as cholesterol in amounts of up to 50% w/w is disclosed in WO-A-9115244 and WO-A-9409829, whilst the incorporation of at least a small amount (e.g. ca. 1 mole %) of negatively charged lipid (e.g. phosphatidylserine or a fatty acid) to enhance stability is suggested in WO-A-9222247. A preferred phospholipid composition according to WO-A-9428780 comprises dipalmitoylphosphatidylcholine, polyethyleneglycol 5000-substituted dipalmitoylphosphatidylethanolamine and dipalmitoylphosphatidic acid in molar proportions of about 87:8:5. Typical mixed phospholipid compositions according to WO-A-9409829 and WO-A-9516467 comprise diarachidoylphosphatidylcholine and dipalmitoylphosphatidic acid in weight proportions of about 100:4, although the latter specification also exemplifies use of equal amounts by weight of distearoylphosphatidylcholine and dipalmitoylphosphatidylglycerol.

It will be apparent from the foregoing that in existing phospholipid-containing microbubble suspensions proposed for use as contrast media, at least 50% of the phospholipid content comprises neutral phospholipids such as lecithins. Most commonly only a minor proportion, e.g. ca. 5%, of charged phospholipids is present.

The present invention is based on the finding that the use of predominantly charged phospholipids as essentially the sole amphiphilic component of microbubble-containing contrast agents may convey valuable and unexpected benefits in terms of parameters such as product stability and acoustic properties. Whilst we do not wish to be bound by theoretical considerations it is believed that electrostatic repulsion between charged phospholipid membranes encourages the formation of stable and stabilising monolayers at microbubble-carrier liquid interfaces; the flexibility and deformability of such thin membranes will enhance the echogenicity of products according to the invention relative to gas-filled liposomes comprising one or more lipid bilayers.

We have also found that the use of charged phospholipids may enable the provision of microbubble contrast agents with advantageous properties regarding, for example, stability, dispersibility and resistance to coalescence without recourse to additives such as further surfactants and/or viscosity enhancers, thereby ensuring that the number of components administered to the body of a subject upon injection of the contrast agents is kept to a minimum. Thus, for example, the charged surfaces of the microbubbles may minimise or prevent their aggregation as a result of electrostatic repulsion.

BRIEF DESCRIPTION OF THE DRAWING

FIG. 1.1 of the drawing is a plot of the percentage survival of the volume concentration of microbubbles surviving lyophilisation against the relative amount of charged phospholipid in the microbubble-stabilising phospholipid membranes.

Thus, according to one embodiment of the present invention, there is provided a contrast agent for use in diagnostic studies comprising a suspension in an injectable aqueous carrier liquid of gas microbubbles stabilised by phospholipid-containing amphiphilic material characterised in that said amphiphilic material consists essentially of phospholipid predominantly comprising molecules with net charges.

Desirably at least 75%, preferably substantially all of the phospholipid material in the contrast agents of the invention consists of molecules which individually bear a net overall charge under conditions of preparation and/or use, which charge may be positive or, more preferably, negative. Representative positively charged phospholipids include esters of phosphatidic acids such as dipalmitoylphosphatidic acid or distearoylphosphatidic acid with aminoalcohols such as hydroxyethylenediamine. Examples of negatively charged phospholipids include naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins. The fatty acyl groups of such phospholipids will typically each contain about 14–22 carbon atoms, for example as in palmitoyl and stearoyl groups. Lyso forms of such charged phospholidids are also useful in accordance with the invention, the term "lyso" denoting phospholipids containing only one fatty acyl group, this preferably being ester-linked to the 1-position carbon atom of the glyceryl moiety. Such lyso forms of charged phospholipids may advantageously be used in admixture with charged phospholipids containing two fatty acyl groups.

Phosphatidylserines represent particularly preferred phospholipids of use in contrast agents according to the invention and preferably constitute a substantial part, e.g. at least 80% of the initial phospholipid content thereof, for example 85–92%, although this may subsequently be reduced somewhat, e.g. to ca. 70%, in subsequent processing such as heat sterilisation. While we do not wish to be bound by theoretical considerations, it may be that ionic bridging between the carboxyl and amino groups of adjacent serine moieties contributes to the stability of such systems. Preferred phosphatidylserines include saturated (e.g. hydrogenated or synthetic) natural phosphatidylserine and synthetic or semisynthetic dialkanoylphosphatidylserines such as distearoylphosphatidylserine, dipalmitoylphosphatidylserine and diarachidoylphosphatidylserine.

An important advantage of the use of such phosphatidylserine-based contrast agents is that the body recognises aged red blood cells and platelets by high concentrations of phosphatidylserine on their surface and so may eliminate such contrast agents from the blood stream in a manner similar to the elimination of red blood cells. Furthermore, since the surface of such contrast agents may be registered as endogenous by the body, they may avoid induction of adverse systemic side effects such as haemodynamic effects and other anaphylactic reactions which may accompany administration of some liposome preparations (see e.g. WO-A-9512386). In support of this, no acute toxic effects such as changes in blood pressure or heart rate have been observed in animal tests on dogs injected with intravenous boluses of contrast agents according to the invention at doses of up to ten times a normal imaging dose.

Any biocompatible gas may be employed in the contrast agents of the invention, it being appreciated that the term "gas" as used herein includes any substances (including mixtures) substantially or completely in gaseous (including vapour) form at the normal human body temperature of 37° C. The gas may thus, for example, comprise air; nitrogen; oxygen; carbon dioxide; hydrogen; nitrous oxide; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. At least some of the halogen atoms in halogenated gases advantageously are fluorine atoms. Thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perflucromethylcyclopentane, perfluorodimethylcyclopentanes, perfluorocyclohexane, perfluoromethylcyclohexane and perfluorocycloheptane. Other halogenated gases include fluorinated, e.g. perfluorinated, ketones such as perfluoroacetone and fluorinated, e.g. perfluorinated, ethers such as perfluorodiethyl ether.

It may be advantageous in contrast agents of the invention to employ fluorinated gases such as sulphur fluorides or fluorocarbons (e.g. perfluorocarbons) which are known to form particularly stable microbubble suspensions (see, for example, the article by Schneider et al. referred to above). Gas mixtures based on considerations of partial pressures both inside and outside the microbubbles and consequent osmotic effects on microbubble size, e.g. as described in WO-A-9503835, may if desired be employed, for example a mixture of a relatively blood-soluble gas such as nitrogen or air and a relatively blood-insoluble gas such as a perfluorocarbon.

We have found, however, that contrast agents of the invention, for example comprising microbubbles of a perfluoroalkane such as perfluorobutane stabilised by phosphatidylserine, are surprisingly stable in size following intravenous administration to a subject, and do not exhibit the previously described tendency of microbubbles of such gases to grow uncontrollably as a result of inward diffusion of blood gases such as oxygen, nitrogen and carbon dioxide, instead rapidly reaching a maximum size beyond which further growth is not observed. This avoidance of unlimited size increases which could lead to undesirable and potentially highly dangerous blocking of blood vessel capilliaries is a major advantage of contrast agents according to the invention The contrast agents of the invention may be used in a variety of diagnostic imaging techniques, including scintigraphy, ultrasound, MR and X-ray imaging. Their use in diagnostic ultrasound imaging and in MR imaging, e.g. as susceptibility contrast agents, constitute preferred features of the invention.

In vivo ultrasound tests in dogs have shown that contrast agents according to the invention may produce an increase in backscattered signal intensity from the myocardium of 15–25 dB following intravenous injection of doses as low as 1–20 nl microbubbles/kg body weight. Signals may be observed at even lower doses using more sensitive techniques such as colour Doppler or Doppler-derived techniques, e.g. amplitude based Doppler or non-linear techniques such as are described by Tucker et al. in Lancet (1968) p.1253, by Miller in Ultrasonics (1981) pp. 217–224, and by Newhouse et al. in J. Acoust. Soc. Am. 75, pp.1473–1477 (1984). At these low doses attenuation in blood-filled compartments such as the heart chambers has been found to be sufficiently low to permit visualisation of regions of interest in the myocardial vasculature. Tests have also shown such intravenously injected contrast agents to be distributed throughout the whole blood pool, thereby enhancing the echogenicity of all vascularised tissues, and to be recirculated. They have also been found useful as general Doppler signal enhancement aids, and may additionally be useful in ultrasound computed tomography and in physiologically triggered or intermittent imaging.

For ultrasound applications such as echocardiography, in order to permit free passage through the pulmonary system and to achieve resonance with the preferred imaging frequencies of about 0.1–15 MHz, it may be convenient to employ microbubbles having an average size of 0.1–10 $\mu$m, e.g. 1–7 $\mu$m. We have found that contrast agents according to the invention may be produced with a very narrow size distribution for the microbubble dispersion within the range preferred for echocardiography, thereby greatly enhancing their echogenicity as well as their safety in vivo, and rendering the contrast agents of particular advantage in applications such as blood pressure measurements, blood flow tracing and ultrasound tomography. Thus, for example, products in which over 90% (e.g. at least 95%, preferably at least 98%) of the microbubbles have diameters in the range 1–7 $\mu$m and less than 5% (e.g. not more than 3%, preferably not more than 2%) of the microbubbles have diameters above 7 $\mu$m may readily be prepared.

In such ultrasound applications the contrast agents of the invention may, for example, be administered in doses such that the amount of phospholipid injected is in the range 0.1–10 $\mu$g/kg body weight, more preferably 1–5 $\mu$g/kg. It will be appreciated that the use of such low levels of phospholipid is of substantial advantage in minimising possible toxic side effects.

In general we have found it unnecessary to incorporate additives such as emulsifying agents and/or viscosity enhancers which are commonly employed in many existing contrast agent formulations into contrast agents of the invention. As noted above this is of advantage in keeping to a minimum the number of components administered to the body of a subject and ensuring that the viscosity of the contrast agents is as low as possible. Since preparation of the contrast agents typically involves a freeze drying step as discussed in further detail hereinafter it may, however, be advantageous to include one or more agents with cryoprotective and/or lyoprotective effects and/or one or more bulking agents, for example an alcohol, e.g. an aliphatic alcohol such as t-butanol; a polyol such as glycerol; an aminoacid such as glycine; a carbohydrate, e.g. a sugar such as sucrose, mannitol, trehalose, glucose, lactose or a cyclodextrin, or a polysaccharide such as dextran; or a polyglycol such as polyethylene glycol. A substantial list of agents with cryoprotective and/or lyoprotective effects is given in Acta Pharm. Technol. 34(3), pp. 129–139 (1988), the contents of which are incorporated herein by reference. The use of physiologically well-tolerated sugars such as sucrose, e.g. in an amount such as to render the product isotonic or somewhat hypertonic, is preferred.

Prior art microbubble-containing contrast agents, for example as described in WO--A-9409829, are typically prepared by contacting powdered surfactant, e.g. freeze-dried preformed liposomes or freeze-dried or spray-dried phospholipid solutions, with air or other gas and then with aqueous carrier, agitating to generate a microbubble suspension which must then be administered shortly after its preparation. Such processes, however, suffer the disadvantages that substantial agitational energy must be imparted to generate the required dispersion and that the size and size distribution of the microbubbles are dependent on the amount of energy applied and so cannot in practice be controlled.

We have now found that contrast agents according to the invention may advantageously be prepared by generating a gas microbubble dispersion in an appropriate phospholipid-containing aqueous medium, which may if desired previously have been autoclaved or otherwise sterilised, and thereafter subjecting the dispersion to lyophilisation to yield a dried reconstitutable product. Such products, e.g. comprising the lyophilised residue of a suspension of gas microbubbles in an amphiphilic material-containing aqueous medium wherein the amphiphilic material consists essentialy of phospholipid predominantly comprising molecules which individually have an overall net charge, constitute a further feature of the present invention. Where the dried product contains one or more cryoprotective and/or lyoprotective agents it may, for example, comprise a microbubble-releasing cryoprotectant and/or lyoprotectant (e.g. carbohydrate) matrix containing gas-filled substantially spherical cavities or vacuoles surrounded by layers of the amphiphilic material.

More particularly we have found that dried products so prepared are especially readily reconstitutable in water or an aqueous solution such as saline (which may advantageously be balanced so that the final product for injection is not hypotonic), requiring only minimal agitation such as may, for example, be provided by gentle hand-shaking. The size of the microbubbles so generated is consistently reproducible and in practice is independent of the amount of agitational energy applied, being determined by the size of the microbubbles formed in the initial microbubble dispersion, this size parameter surprisingly being substantially maintained in the lyophilised and reconstituted product. Thus, since the size of the microbubbles in the initial dispersion may readily be controlled by process parameters such as the method, speed and duration of agitation, the final microbubble size may readily be controlled.

Lryophilised products according to the invention have proved to be storage stable for several months under ambient conditions. The microbubble dispersions generated upon reconstitution in water are stable for at least 12 hours, permitting considerable flexibility as to when the dried product is reconstituted prior to injection.

The above-described process for the preparation of contrast agents according to the invention is generally applicable to the preparation of contrast agents comprising suspensions in an injectable aqueous carrier liquid of gas microbubbles stabilised by membrane-forming lipids, including both neutral and charged lipids (e.g. phospholipids) as well as mixtures thereof. Such a process, comprising the steps:

i) generating a dispersion of gas microbubbles in an aqueous medium containing a membrane-forming lipid;

ii) lyophilising the thus-obtained lipid-stabilised gas dispersion to yield a dried lipid product; and iii) reconstituting the said dried product in an injectable carrier liquid, constitutes a further feature of the present invention, as does a reconstitutable dried product obtainable in accordance with steps (i) and (ii) of this process, for example a product comprising a microbubble releasing matrix (e.g. of cryoprotectant/lyoprotectant) containing gas-filled substantially spherical cavities or vacuoles surrounded by layers of membrane-forming lipid material.

Step (i) may, for example, be effected by subjecting the lipid-containing aqueous medium to any appropriate emulsion-generating technique, for example sonication, shaking, high pressure homogenisation, high speed stirring or high shear mixing, e.g. using a rotor-stator homogeniser, in the presence of the selected gas. The aqueous medium may, if desired, contain additives which serve as viscosity enhancers and/or as solubility aids for the lipid, such as alcohols or polyols, e.g. glycerol and/or propylene glycol.

The gas employed in the emulsification step need not be that desired in the final product. Thus most of this gas content may be removed during the subsequent lyophilisation step and residual gas may be removed by evacuation of the dried product, to which an atmosphere or overpressure of the desired end product gas may then be applied. The emulsification gas may therefore be selected purely to optimise the emulsification process parameters, without regard to end product considerations. We have found emulsification in the presence of a sulphur fluoride such as sulphur hexafluoride or a fluorinated low molecular weight hydrocarbon gas such as a perflucroalkane or perfluorocycloalkane, preferably containing 4 or 5 carbon atoms, to be particularly advantageous in terms of ultimately yielding end products with consistent and narrowly distributed microbubble sizes.

The emulsification is conveniently effected at about ambient temperature, e.g. at ca. 25±10° C. It may be necessary initially to heat the aqueous medium to facilitate hydration and thus dispersion of the phospholipid and then allow it to equilibrate to ambient temperature prior to emulsification.

Gas dispersions obtainable according to step (i), especially aqueous dispersions of gas microbubbles stabilised by amphiphilic material consisting essentially of phospholipid predominantly comprising molecules which individually have an overall net charge, constitute a feature of the invention. Such dispersions, e.g. in which the amphiphilic material comprises one or more phosphatidylserines such as dialkanoylphosphatidylserines, and especially which contain gases having low water solubility (e.g. sulphur hexafluoride or perfluoroalkanes such as perfluorobutanes), are useful intermediates in, for example, the manufacture of the above-described dried products and of contrast agents in which the amphiphilic material is crosslinked or polymerised. It will be appreciated that such dispersions, if prepared in physiologically acceptable form, e.g. in a sterile aqueous carrier liquid such as sterile pyrogen-free water or saline, will themselves be contrast agents in accordance with the invention. Dispersions produced according to step (i) may advantageously be subjected to one or more washing steps prior to contrast agent use or to lyophilisation step (ii), in order to separate and remove additives such as viscosity enhancers and solubility aids, as well as unwanted material such as non-gas-containing colloidal particles and undersized and/or oversized microbubbles. Such washing may be effected in per se known manner, the microbubbles being separated using techniques such as flotation or centrifugation. The ability to remove additives in this way and also to obtain microbubble dispersions with a particularly narrow size distribution represent important advantages of the process of the invention especially since, as noted above, the resulting size distribution is substantially retained after lyophilisation and reconstitution. Accordingly it is particularly preferred to use a process comprising gas dispersion, washing/separation, lyophilisation and reconstitution steps.

Size-fractionated microbubble dispersions may be prepared wherein at least 90% of the microbubbles have sizes within a 2 $\mu$m range, the microbubbles preferably having a volume mean diameter within the range 2–5 $\mu$m. Such dispersions and frozen and lyophilised products derived therefrom, e.g. as described hereinafter, represent preferred features of the invention.

Where one or more cryoprotective and/or lyoprotective agents are employed these may advantageously be added after the washing steps, prior to lyophilisation.

Lyophilisation of the gas dispersion may, for example, be effected by initially freezing it and thereafter lyophilising the frozen gas dispersion, for example in per se generally known manner. Such frozen gas dispersions, i.e. frozen microbubble-releasing aqueous dispersions comprising gas microbubbles stabilised by amphiphilic material consisting essentially of phospholipid predominantly comprising molecules which individually have an overall net charge, constitute a further feature-of the invention. The microbubbles may preferably be size fractionated prior to freezing, the released microbubbles preferably having a volume mean diameter within the range 2–5 $\mu$m. Such products may be stored frozen and thawed when desired, e.g. by simple warming and/or by addition of a carrier liquid, to regenerate microbubble dispersions useful as contrast agents in accordance with the invention.

Since the dried product will normally be reconstituted in accordance with step (iii) above prior to administration, the gas dispersion may advantageously be filled into sealable vials prior to lyophilisation so as to give vials each containing an appropriate amount, e.g. a single dosage unit, of lyophilised dried product for reconstitution into an injectable form. By lyophilising the gas dispersion in individual vials rather than in bulk, handling of the delicate honeycomb-like structure of the lyophilised product and the risk of at least partially degrading this structure are avoided. Following lyophilisation and any optional further evacuation of gas and introduction into the headspace of gas desired to be present as microbubbles in the ultimately formulated contrast agent, the vials may be sealed with an appropriate closure. It will be appreciated that the ability to select the end product gas content, coupled with the ability independently to control the end product microbubble size by selection of appropriate process parameters during the initial dispersion step and any ensuing washing/separation step, enable the independent selection of microbubble size and gas content, thereby permitting the products to be matched to particular applications.

In general the frozen gas dispersion or the dried product from step (ii), e.g. after any necessary and/or desired supplementation or exchange of gas content, may be reconstituted by addition of an appropriate injectable carrier liquid such as sterile pyrogen-free water or saline for injection. Where the dried product is contained in a vial this is conveniently sealed with a septum through which the carrier liquid may be injected using a syringe. It may be advantageous to mix or gently shake the product following reconstitution. However, as noted above, in the stabilised contrast agents according to the invention the size of the gas microbubbles may be substantially independent of the amount of agitational energy applied to the reconstituted dried product. Accordingly no more than gentle hand-shaking may be required to give reproducible products with consistent microbubble size.

The following non-limitative Examples serve to illustrate the invention.

EXAMPLE 1

Dispersions of microbubbles stabilised by different phospholipids or phospholipid mixtures are made according to the general procedure described below, using the process parameters given in Table 1.1 below.

Solutions of the selected phospholipids or phospholipid mixtures in water containing 5.4% (w/w) of a mixture of propylene glycol and glycerol (3:10 w/w) giving a phospholipid concentration of 2–5 mg/ml are prepared (for phosphatidylethanolamine the water is adjusted to pH=10.5 with sodium hydroxide), the phospholipids being hydrated by ultrasonic treatment and/or heating to approximately 80OC for the stated time (Table 1.1) and cooled to room temperature prior to use. A given volume of this solution is divided between several 2 ml chromatography vials, using 0.8–1 ml solution per vial. The head space of each vial is filled with perfluorobutane gas, and the vials are securely capped and shaken for 45 seconds using an Espe CapMix® (mixer for dental materials). The resulting microbubble dispersions are transferred to a larger vial and centrifuged at 2000 rpm for 5 minutes, giving a turbid infranatant below a floating layer of microbubbles. The infranatant is removed by a syringe and replaced with an equal volume of water at neutral pH. The washing step is repeated, but now the infranatant is replaced by 10% (w/w) sucrose. 2 ml portions of the washed dispersion are divided between 10 ml flat-bottomed vials specially designed for lyophilisation, and the vials are cooled to –47° C. and lyophilised for approximately 48 hours, giving a white fluffy solid substance. The vials are transferred to a vacuum chamber, and air is removed by a vacuum pump and replaced by perfluorobutane gas. Prior to use, water is added and the vials are gently hand-shaken for several seconds, giving microbubble dispersions suitable as ultrasound contrast agents.

The size distribution and volume concentration of the microbubbles are measured using a Coulter Counter Mark II apparatus fitted with a 50 μm aperture with a measuring range of 1–30 μm. 20 μl samples are diluted in 200 ml saline saturated with air at room temperature and allowed to equilibrate for 3 minutes prior to measurement. The measurements are made on microbubble dispersions prior to lyophilisation (washed bubble dispersion) and after lyophilisation (reconstituted with water to the same volume as before lyophilisation). The data is presented in Table 1.2 below.

Figure 11:
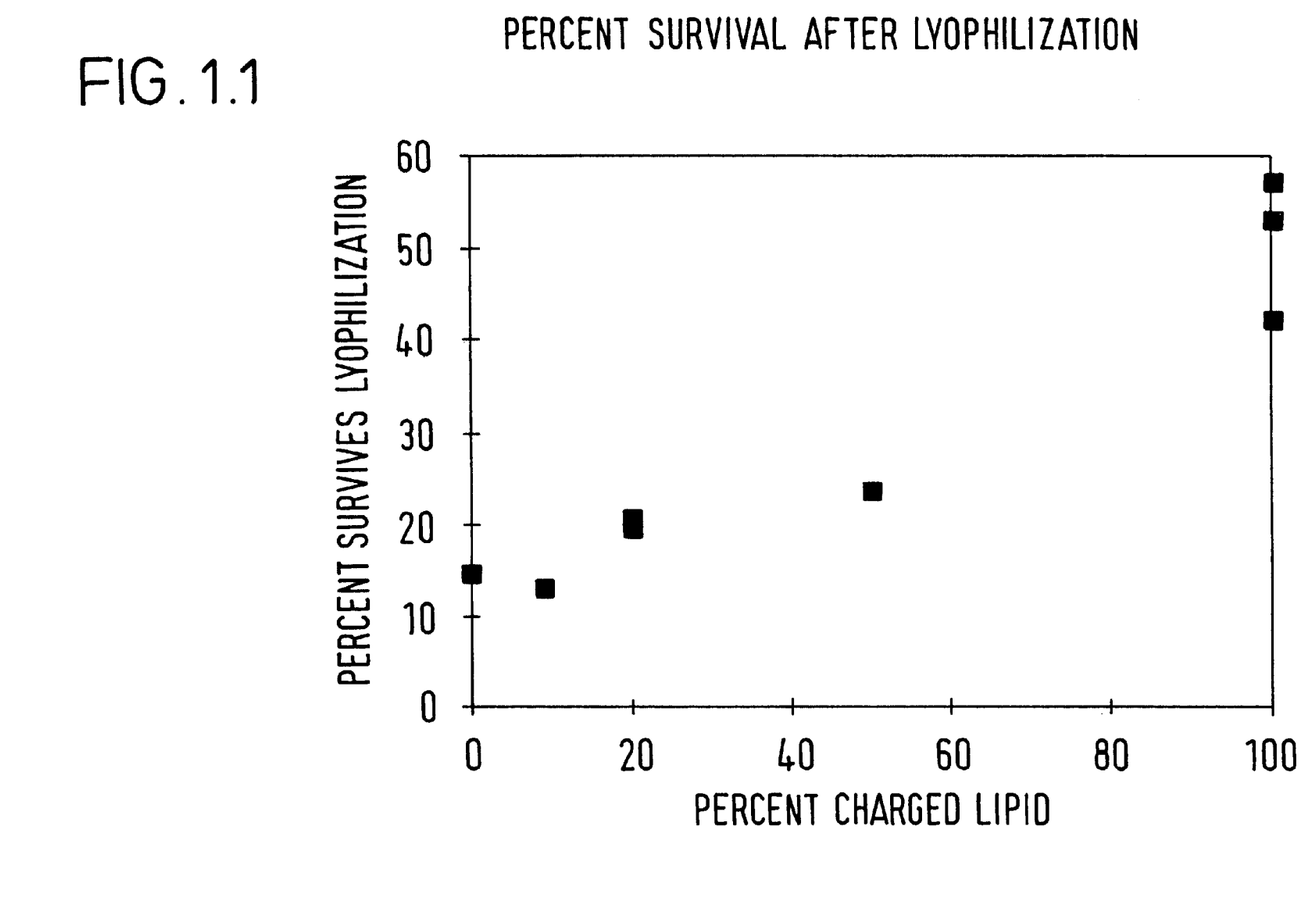

The efficiency of lyophilisation for the different phospholipid stabilised microbubble dispersions is calculated as the percentage survival of the volume concentration following lyophilisation and reconstitution. A plot (see FIG. 1.1 of the drawing) shows how this parameter varies with the relative amount of charged phospholipid in the membrane. As can be seen, the efficiency of lyophilisation increases with increased amount of charged phospholipid in the membrane, being highest for membranes containing charged phospholipids only.

TABLE 1.1

Composition and process parameters used in production of phospholipid stabilised perfluoro-n-butane gas bubble dispersions as described in Example 1.

| PLs and ratios (by weight) | Amount PL [mg/ml] | Amount aqueous solvent [ml] | Sonication bath [min] | Heat treatment [min] | Batch size [ml] | Vol. per vial [ml] |
|---|---|---|---|---|---|---|
| DPPE | 20 | 10 | — | 30 | 10 | 0.8 |
| H-PC/H-PS (9:1) | 45.5 | 9.1 | 10 | 2 | 9 | 0.9 |
| H-PC/H-PS (4:1) | 14.0 | 7 | 10 | 2 | 7 | 1 |
| DSPC/DSPS (4:1) | 10.4 | 5.2 | 10 | 2 | 4 | 1 |
| DSPC/DSPG (1:1) | 15.2 | 7.6 | 10 | 2 | 7 | 1 |
| DPPS | 24.9 | 12.5 | — | 30 | 11 | 1 |
| DSPS | 24.8 | 12.5 | — | 30 | 11 | 1 |
| DSPG/DPPA (10:1) | 20.2 | 10 | — | 10 | 10 | 0.8 |
| DSPG/DPPA (1:1) | 52.0 | 10.4 | — | 10 | 8 | 0.8 |

Legend:
PL = phospholipid
DPPE = dipalmitoylphosphatidylethanolamine
H-PC = hydrogenated egg phosphatidylcholine
H-PS = hydrogenated egg phosphatidylserine
DSPC = distearoylphosphatidylcholine
DSPS = distearoylphosphatidylserine
DSPG = distearoylphosphatidylglycerol
DPPS = dipalmitoylphosphatidylserine
DPPA = dipalmitoylphosphatidic acid.

TABLE 1.2

Yield measured as volume concentration of bubbles (in percent of total dispersion volume) (i) after washing the dispersion and (ii) after lyophilisation and reconstitution.

| PLs and ratios (by weight) | % charged lipid in membrane | Vol. conc. (%) prior to lyophilisation | Vol. conc. (%) after lyophilisation | Amount surviving lyophilisation [% initial vol. conc.] |
|---|---|---|---|---|
| DPPE | 0 | 0.7 | 0.1 | 16.4 |
| H-PC/H-PS (9:1) | 10 | 6.4 | 0.9 | 14.1 |
| H-PC/H-PS (4:1) | 20 | 1.0 | 0.2 | 20.0 |
| DSPC/DSPS (4:1) | 20 | 4.8 | 1.0 | 20.8 |
| DSPC/DSPG (1:1) | 50 | 0.3 | 0.1 | 33.3 |
| DPPS | 100 | 0.7 | 0.4 | 57.1 |
| DSPS | 100 | 1.0 | 0.5 | 50.0 |
| DSPG/DPPA (10:1) | 100 | 1.4 | 0.7 | 52.9 |
| DSPG/DPPA (1:1) | 100 | 4.3 | 1.8 | 41.9 |

Legend: See Table 1.1

EXAMPLE 2 a) Preparation of Microbubble Dispersions by Shaking 25.3 mg hydrogenated egg phosphatidylserine is added to 12.5 ml water containing 5.4% (w/w) of a mixture of propylene glycol and glycerol (3:10 w/w). The phospholipid material is hydrated by heating to 70° C. for approximately 30 minutes, followed by cooling to room temperature. 11 ml of the dispersion is divided in 1 ml portions between eleven 2 ml vials, and the head space of the vials is filled with perfluoro-n-butane gas. The vials are securely capped and shaken for 45 seconds using an Espe CapMix® (mixer for dental materials). The resulting microbubble dispersions are combined in four larger vials and centrifuged at 2000 rpm for 5 minutes, giving a turbid infranatant below a floating layer of microbubbles. The infranatant is removed by a syringe and replaced with an equal volume of water at neutral pH. The washing step is repeated, but now the infranatant is replaced by 10% (w/w) sucrose. 2 ml portions of the resulting dispersion are divided between 10 ml flat-bottomed vials specially designed for lyophilisation, and the vials are cooled to −47° C. and lyophilised for approximately 48 hours, giving a white fluffy solid substance. The vials are transferred to a vacuum chamber, and air is removed by a vacuum pump and replaced by perfluoro-n-butane gas. Prior to use, water is added and the vials are gently hand-shaken for several seconds, giving microbubble dispersions suitable as ultrasound contrast agents.

b) Preparation of Microbubble Dispersions by Rotor Stator Mixing 500.4 mg hydrogenated egg phosphatidylserine is added to 100 ml water containing 5.4% (w/w) of a mixture of propylene glycol and glycerol (3:10 w/w). The mixture is shaken and heated to 80° C. for five minutes, allowed to cool to room temperature, shaken again and left standing overnight prior to use.

50 ml of the resulting solution is transferred to a round-bottomed flask with a conical neck. The flask is fitted with a glass jacket having a temperature control inlet and outlet connected to a water bath maintained at 25° C. A rotor stator mixing shaft is introduced into the solution and to avoid gas leakage the space between the neck wall and the mixing shaft is sealed with a specially designed metal plug fitted with a gas inlet/outlet connection for adjustment of gas content and pressure control. The gas outlet is connected to a vacuum pump and the solution is degassed for one minute. An atmosphere of perfluoro-n-butane gas is then applied through the gas inlet.

The solution is homogenised at 23000 rpm for 10 minutes, keeping the rotor stator mixing shaft such that the openings are slightly above the surface of the liquid. A white coloured creamy dispersion is obtained, which is transferred to a sealable container and flushed with perfluoro-n-butane. The dispersion is then transferred to a separating funnel and centrifuged at 12000 rpm for 30 minutes, yielding a creamy layer of bubbles at the top and a turbid infranatant. The infranatant is removed and replaced with water. The centrifugation is then repeated twice, but now at 12000 rpm for 15 minutes. After the last centrifugation, the supernatant is replaced by 10% (w/w) sucrose. 2 ml portions of the resulting dispersion are divided between 10 ml flat-bottomed vials specially designed for lyophilisation, and the vials are cooled to −47° C. and lyophilised for approximately 48 hours, giving a white fluffy solid substance. The vials are now transferred to a vacuum chamber, and air is removed by a vacuum pump and replaced by perfluoro-n-butane gas. Prior to use, water is added and the vials are gently hand-shaken for several seconds, giving microbubble dispersions suitable as ultrasound contrast agents.

c) Preparation of Microbubble Dispersions by Sonication 500.4 mg hydrogenated egg phosphatidylserine is added to 100 ml water containing 5.4% (w/w) of a mixture of propylene glycol and glycerol (3:10 w/w). The mixture is shaken and heated to 80° C. for five minutes, allowed to cool to room temperature, shaken again and left standing overnight prior to use.

This solution is pumped through a 4 ml sonicator flow-through cell and exposed to ultrasound at 20 kHz with an amplitude of 90 $\mu$m. The diameter of the sonicator horn is 1.3 cm, the inner diameter of the cell is 2.1 cm and the distance between the horn and the bottom of the cell is 1 cm. The lipid solution is mixed with perfluoro-n-butane at a ratio of 1:2 v/v before it enters the sonicator cell (20 ml/min lipid solution and 40 ml/min perfluoro-n-butane gas). The temperature is kept at 33° C. A white and creamy dispersion is obtained which is filled into a container and flushed with perfluoro-n-butane.

Characterisation

The size distribution and volume concentration of the microbubbles are measured using a Coulter Counter Mark II apparatus fitted with a 50 $\mu$m aperture with a measuring range of 1–30 $\mu$m. 20 $\mu$l samples are diluted in 200 ml saline saturated with air at room temperature, and allowed to equilibrate for 3 minutes prior to measurement.

Ultrasound characterisation is performed on a experimental set up slightly modified from de Jong, N. and Hoff, L. as described in "Ultrasound scattering properties of Albunex microspheres", Ultrasonics 31(3), pp. 175–181 (1993). This instrumentation measures the ultrasound attenuation efficacy in the frequency range 2–8 MHz of a dilute suspension of contrast agent. During the attenuation measurement a pressure stability test is performed by exposing the sample to an overpressure of 120 mmHg for 90 seconds. Typically 2–3 $\mu$l of sample is diluted in 55 ml Isoton II and the diluted sample suspension is stirred for 3 minutes prior to analysis. As primary response parameter the attenuation at 3.5 MHz is used, together with the recovery attenuation value at 3.5 MHz after release of the overpressure.

TABLE 2.1

In vitro characteristics of bubble dispersions produced according to Example 2(a)–(c). Number and volume weighted concentrations and volume mean diameters. Acoustic properties measured according to description above.

| Production method (Example No.) | Number conc. [10⁶/ml] | Vol. conc. [%] | Vol. mean diam. [$\mu$m] | Atten. at 3.5 Mhz [dB/cm] | Survival after over-pressure [%] | Freq. at max. atten. [MHz] |
|---|---|---|---|---|---|---|
| 2(a) | 1519 | 1.45 | 3.91 | 30.46 | 100 | 4.1 |
| 2(b) | 10518 | 6.51 | 3.16 | 150.4 | 96 | 4.3 |
| 2(c) | 23389 | 9.57 | 3.83 | 117 | 100 | 3.5 |

EXAMPLE 3

The gas contents of five samples prepared according to Example 2(b) above are replaced with air, perfluorobutane, sulphur hexafluoride, trifluoromethylsulphur pentafluoride and tetramethylsilane respectively, according to the following procedure:

Two samples containing lyophilised product from Example 2(b) are placed in a desiccator having a gas inlet and a gas outlet. The desiccator is connected to a Büchi 168 vacuum/distiller controller which permits controlled evacuation of the samples and inlet of a selected gas. The samples are evacuated at approximately 10 mbar for 5 minutes, whereafter the pressure is increased to atmospheric by inlet of the selected gas, followed by careful capping of the vials. The procedure is repeated using further pairs of samples for each of the selected gases. 2 ml distilled water is added to each vial and the vials are gently hand-shaken prior to use. The resulting microbubble dispersions are characterised with respect to size distribution measurements as described in Example 2. The results are summarised in Table 3.1.

TABLE 3.1

In vitro characteristics of phosphatidylserine-stabilised microbubble dispersions produced according to Example 3 - number and volume weighted concentrations and volume mean diameters.

| Gas | Number conc. [10⁶/ml] | Number mean diam. [$\mu$m] | Vol. conc. [%] | Vol. mean diam. [$\mu$m] |
|---|---|---|---|---|
| Perfluorobutane | 9756 | 1.8 | 4.9 | 5.8 |
| Trifluoromethyl-sulphur pentafluoride | 10243 | 1.9 | 5.9 | 3.5 |
| Sulphur hexafluoride | 9927 | 1.9 | 5.7 | 3.2 |
| Tetramethylsilane | 9947 | 1.9 | 6.1 | 3.7 |
| Air | 9909 | 1.9 | 6.4 | 4.0 |

As will be seem from the above results there is no significant change in size distribution upon gas exchange, demonstrating that the preformed microbubble size is substantially preserved during both lyophilisation and reconstitution.

In vivo Results

One batch prepared with each of the five gases is evaluated in vivo for Doppler enhancement properties at 10 MHz. The dispersions are injected into chinchilla rabbits via an ear vein and measured using a Doppler technique where an ultrasound probe is placed directly on a carotid artery. Signal intensities and duration are recorded and the integral of the Doppler curve is calculated. The results obtained (see Table 3.2 below) show that microbubbles containing perfluorobutane give the strongest Doppler intensity enhancement. Microbubbles containing sulphur hexafluoride, trifluoromethylsulphur pentafluoride or tetramethylsilane are only slightly less efficacious as Doppler enhancers than those containing perfluorobutane, giving integrals in the range 60–80% of the figure for perfluorobutane.

TABLE 3.2

Results for i.v. injections of Example 3 products into rabbits. The values are adjusted for drift in baseline. The Doppler unit is defined as the increase in Doppler signal relative to that of blood.

| Gas | Integrated Arterial Doppler Enhancement (NDU.s) |
| --- | --- |
| Perfluorobutane* | 10361 |
| Trifluoromethylsulphur pentafluoride | 8006 |
| Tetramethylsilane | 6370 |
| Sulphur hexafluoride | 6297 |
| Air | 1024 |

*Average of two injections

EXAMPLE 4

250 mg hydrogenated egg phosphatidylserine is added to 50 ml water for injection containing 5.4% (w/w) of a mixture of propylene glycol and glycerol (7:20 w/w). The mixture is shaken and heated to 80° C. for five minutes, allowed to cool to room temperature, shaken again and left standing overnight prior to use.

100 ml of the resulting solution is transferred to a round-bottomed flask with a conical neck and processed according to the procedure described in Example 2(b). A white coloured creamy dispersion is formed. This dispersion is transferred to a separating funnel and centrifuged at 12000 rpm for 30 minutes, yielding a creamy layer of microbubbles at the top and a turbid infranatant. The infranatant is removed and replaced with 50 ml water for injection. The centrifugation is then repeated twice, but now at 12000 rpm for 15 minutes. To 6 ml of the resulting dispersion is added 6 ml 30% (w/w) trehalose; 2 ml portions of this dispersion are divided between 10 ml flat-bottomed vials specially designed for lyophilisation, and the vials are cooled to −47° C. and stored at this temperature for one day.

Half of the vials are thawed after one day at −47° C., giving homogeneous creamy white dispersions of gas microbubbles suitable as ultrasound contrast agents. The thawed dispersions are characterised by measuring size distribution as described in Example 2 above (see Table 4.1). The remaining vials are lyophilised for approximately 48 hours, giving a white fluffy solid substance. The vials are transferred to a vacuum chamber, and air is removed by a vacuum pump and replaced by perfluoro-n-butane gas. Prior to use, water is added and the vials are gently hand-shaken for several seconds, giving bubble dispersions suitable as ultrasound contrast agents. The reconstituted products are characterised by measuring size distribution and acoustic attenuation using the methods as described in Example 2 above. The results are presented in Table 4.1.

TABLE 4.1

Bubble concentration, size data and acoustic data of perfluoro-n-butane gas bubble dispersions stabilised by hydrogenated phosphatidylserine, treated by freeze - thawing and lyophilisation.

| Sample treatment | Number conc. [$10^6$/ml] | Vol. conc. [%] | Vol. mean diam. [$\mu$m] | Atten. at 3.5 Mhz [dB/cm] | Survival after over-pressure [%] | Freq. at max. atten. [MHz] |
| --- | --- | --- | --- | --- | --- | --- |
| Washed | 10390 | 10.4 | 3.8 | n.a. | n.a. | n.a. |
| Freeze-thawed | 10142 | 9.9 | 3.6 | n.a. | n.a. | n.a. |
| Lyophilised | 7780 | 4.6 | 3.1 | 58.0 | 89 | 5.3 |

Legend:
n.a. = not analysed

EXAMPLE 5

A vial containing lyophilised material under an atmosphere of perfluorobutane is prepared as described in Example 2(b). Water is added to the vial just before use to give a microbubble suspension.

200 ml Isoton II fluid is exposed to air for several days at room temperature to give a fully air-saturated solution. Another 200 ml of the fluid is degassed in a vacuum flask at 60° C. for one hour and cooled to room temperature while maintaining the vacuum. Air is admitted to the flask immediately prior to use.

10 $\mu$l portions of the microbubble suspension are added to each of the fluids and the resulting mixtures are incubated for 5 minutes prior to size characterisation (Coulter Multisizer Mark II).

In the degassed environment, where no diffusion of gases from the fluid into the microbubbles is expected, the mean microbubble diameter is 1.77 $\mu$m and 0.25% of the microbubbles are larger than 5 $\mu$m. In the air-saturated fluid the corresponding values are 2.43 $\mu$m and 0.67%; repeated measurements made after a further 5 minutes indicate that the microbubble sizes have reached a stable value.

These findings show that the average diameter of the microbubbles increases by only 37% when they are exposed to an air-saturated fluid analogous to arterial blood, with very few microbubbles reaching a size which might cause blockage of capillary blood vessels. This may be contrasted with the doubling in size of air/perfluorohexane-containing microbubbles in a similar environment (i.e. a highly diluted dispersion of microbubbles in water containing dissolved air) reported in Example II of WO-A-9503835.

EXAMPLE 6

Preparation of Perfluorobutane Microbubble Dispersions by Shaking

Dipalmitoylphosphatidylserine (sodium salt) was dissolved in a solution of 50° C. mg of propylene glycol/glycerol (3:10) in 1 ml water to a final concentration of 5 mg phospholipid/ml solution. 0.8 ml portions of this stock solution were transferred to 2 ml vials with screw caps, whereafter the head space was flushed with perfluorobutane gas. The vials were vigorously shaken for 45 seconds, and transferred to a table roller for approximately 30 minutes.

EXAMPLE 7

Preparation of Perfluoropentane/Air Microbubble Dispersion by Shaking

A solution of dipalmitoylphosphatidylserine (sodium salt) (5.0 mg) in distilled water (1 ml) in a 2 ml vial with a septum was vigorously shaken for 15 seconds, heated to 60° C. for 10 minutes and then cooled to 20° C. Perfluoropentane (1.2 μl) was added and the vial was vigorously shaken for 30 seconds to give a suspension of perfluoropentane/air microbubbles of size 2–4 μm as determined by light microscopy. This suspension was stable for several days at room temperature.

EXAMPLE 8
Preparation of Perfluoropentane/Air Microbubble Dispersion by Shaking A solution of dipalmitoylphosphatidylserine (sodium salt) (4.6 mg) in distilled water (1 ml) in a 2 ml vial with a septum was vigorously shaken for 15 seconds, heated to 60° C. for 10 minutes and then cooled to 20° C. Perfluoropentane (2.4 μl) was added and the vial was vigorously shaken for 30 seconds to give a suspension of perfluoropentane/air microbubbles of size 2–5 μm as determined by light microscopy. This suspension was stable for several days at room temperature.

EXAMPLE 9

Preparation of Perfluoropentane/Air Microbubble Dispersion by Shaking

A solution of dipalmitoylphosphatidylserine (sodium salt) (5.2 mg) in distilled water (1 ml) in a 2 ml vial with a septum was vigorously shaken for 15 seconds, heated to 60° C. for 10 minutes and then cooled to 20° C. Perfluoropentane (5 mg) was added and the vial was vigorously shaken for 30 seconds to give a suspension of perfluoropentane/air microbubbles of size 2–5 μm as determined by light microscopy. This suspension was stable for several days at room temperature.

EXAMPLE 10
Preparation of Perfluorobutane/Perfluorohexane Microbubble Dispersion by Shaking A solution of dipalmitoylphosphatidylserine (sodium salt) (5.0 mg) in distilled water (1 ml) in a 2 ml vial with a septum was vigorously shaken for 15 seconds, heated to 60° C. for 10 minutes and then cooled to 20° C. The vial was evacuated at 10 mm Hg for 20 minutes to remove air whereafter the headspace was flushed with perfluorobutane. Perfluorohexane (1.4 μl) was added and the vial was vigorously shaken for 30 seconds to give a suspension of perfluorobutane/perfluorohexane microbubbles of size 1–10 μm as determined by light microscopy. This suspension was stable for several days at room temperature.

EXAMPLE 11
Preparation of Perfluoropentane/Air Microbubble Dispersion by Shaking A solution of dipalmitoylphosphatidylserine (sodium salt) (3.0 mg) and propylene glycol/glycerol (3:10, 46 mg) in distilled water (1 ml) in a 2 ml vial with a septum was vigorously shaken for 1 minute. Perfluoropentane (4.5 μl) was added and the vial was vigorously shaken for 30 seconds to give a suspension of perfluoropentane/air microbubbles of size 2–10 μm as determined by light microscopy. This suspension was stable for several hours at room temperature.

EXAMPLE 12
Preparation of Perfluoropentane/Air Microbubble Dispersion by Shaking A solution of dipalmitoylphosphatidylserine (sodium salt) (2.5 mg) and dipalmitoylphosphatidylcholine (0.5 mg) in distilled water (1 ml) was heated at 80° C. for 1 hour. Perfluoropentane (1.2 μl) was then added and the mixture was vigorously shaken for 30 seconds to give a suspension of perfluoropentane/air microbubbles of size 1–8 μm as determined by light microscopy. This suspension was stable for several hours at room temperature.

EXAMPLE 13
Preparation of Perfluoropentane/Air Microbubble Dispersion by Shaking A solution of dipalmitoylphosphatidylserine (sodium salt) (4.5 mg) and dipalmitoylphosphatidylcholine (0.5 mg) in distilled water (1 ml) was heated at 80° C. for 1 hour. Perfluoropentane (1.2 μl) was added and the mixture was vigorously shaken for 30 seconds to give a suspension of perfluoropentane/air microbubbles of size 1–10 μm as determined by light microscopy. This suspension was stable for several hours at room temperature.

EXAMPLE 14
Preparation of Perfluoropentane/Air Microbubble Dispersion by Shaking A solution of dipalmitoylphosphatidylserine (sodium salt) (2.5 mg) and dipalmitoylphosphatidylcholine (0.7 mg) in distilled water (1 ml) was heated at 80° C. for 1 hour. Perfluoropentane (5 mg) was added and the mixture was vigorously shaken for 30 seconds to give a suspension of perfluoropentane/air microbubbles of size 1–8 μm as determined by light microscopy. This suspension was stable for several hours at room temperature.

EXAMPLE 15

Preparation of Perfluoropentane/Air Microbubble Dispersion by Shaking

A solution of dipalmitoylphosphatidylserine (sodium salt) (2.5 mg) and dipalmitoylphosphatidylcholine (0.6 mg) and propylene glycol/glycerol (3:10, 40 mg) in distilled water (1 ml) was heated at 80° C. for 1 hour. Perfluoropentane (1.4 μl) was added and the mixture was vigorously shaken for 30 seconds to give a suspension of perfluoropentane/air microbubbles of size 1–10 μm as determined by light microscopy. This suspension was stable for several hours at room temperature.

EXAMPLE 16
Preparation of Perfluoropentane/Air Microbubble Dispersion by Shaking A solution of dipalmitoylphosphatidylserine (sodium salt) (4.5 mg) and dipalmitoylphosphatidylcholine (1.0 mg) and propylene glycol/glycerol (3:10, 45 mg) in distilled water (1 ml) was heated at 80° C. for 1 hour. Perfluoropentane (1.2 μl) was added and the mixture was vigorously shaken for 30 seconds to give a suspension of perfluoropentane/air microbubbles of size 1–10 μm as determined by light microscopy. This suspension was stable for several hours at room temperature.

EXAMPLE 17

Preparation of Perfluoropentane/Air Microbubble Dispersion by Shaking

A solution of dipalmitoylphosphatidylserine (sodium salt) (2.5 mg), dipalmitoylphosphatidylcholine (0.5 mg) and propylene glycol/glycerol (3:10, 40 mg) in distilled water (1 ml) was heated at 80° C. for 1 hour. Perfluoropentane (2.5 μl) was added and the mixture was vigorously shaken for 30 seconds to give a suspension of perfluoropentane/air microbubbles of size 1–10 μm as determined by light microscopy. This suspension was stable for several hours at room temperature.

EXAMPLE 18
Preparation of Perfluorohexane/Air Microbubble Dispersion by Shaking A solution of dipalmitoylphosphatidylserine (sodium salt) (2.5 mg) and dipalmitoylphosphatidylcholine (0.5 mg) in distilled water (1 ml) was heated at 80° C. for 1 hour. Perfluorohexane (1.4 μl) was added and the mixture was vigorously shaken for 30 seconds to give a suspension of perfluorohexane/air microbubbles of size 2–10 μm as determined by light microscopy. This suspension was stable for several hours at room temperature.

EXAMPLE 19
Preparation of Perfluorohexane/Air Microbubble Dispersion by Shaking A solution of dipalmitoylphosphatidylserine (sodium salt) (2.5 mg) and dipalmitoylphosphatidylcholine (1.3 mg) in distilled water (1 ml) was heated at 80° C. for 1 hour. Perfluorohexane (1.4 μl) was added and the mixture was vigorously shaken for 30 seconds to give a suspension of perfluorohexane/air microbubbles of size 2–10 μm as determined by light microscopy. This suspension was stable for several hours at room temperature.

EXAMPLE 20
Preparation of Perfluorohexane/Air Microbubble Dispersion by Shaking A solution of dipalmitoylphosphatidylserine (sodium salt) (2.5 mg) and dipalmitoylphosphatidylcholine (0.6 mg) and propylene glycol/glycerol (3:10, 45 mg) in distilled water (1 ml) was heated at 80° C. for 1 hour. Perfluorohexane (2.4 μl) was added and the mixture was vigorously shaken for 30 seconds to give a suspension of perfluorohexane/air microbubbles of size 2–10 μm as determined by light microscopy. This suspension was stable for several hours at room temperature.

What is claimed is:

1. A process for the preparation of a microbubble-releasing matrix comprising a cryoprotectant/lyoprotectant containing gas-filled substantially spherical cavities or vacuoles surrounded by layers of membrane-forming lipid material, wherein said gas is selected from the group consisting of sulphur hexafluoride, fluorinated low molecular weight hydrocarbons and mixtures of the foregoing, and wherein at least about 70% of said membrane-forming lipid material consists of one or more phosphatidylserines, said process comprising the steps:
   i) dispersing said gas in an aqueous medium containing said membrane-forming lipid material to form a lipid-stabilised dispersion of microbubbles of said gas;
   ii) adding said cryoprotectant/lyoprotectant to said dispersion; and
   iii) lyophilising said dispersion to yield said microbubble-releasing matrix.

2. A process as claimed in claim 1 wherein said cryoprotectant/lyoprotectant is a carbohydrate.

3. A process as claimed in claim 2 wherein said carbohydrate is sucrose.

4. A process as claimed in claim 1 wherein said gas comprises a perfluorinated low molecular weight hydrocarbon.

5. A process as claimed in claim 4 wherein said perfluorinated low molecular weight hydrocarbon is selected from the group consisting of perfluoropropane, perfluorobutane and perfluoropentane.

6. A process as claimed in claim 1 wherein at least 80% of said membrane-forming lipid material consists of one or more phosphatidylserines.

7. A process as claimed in claim 1 wherein said phosphatidylserine or phosphatidylserines are selected from the group consisting of synthetic phosphatidylserine, semisynthetic phosphatidylserine, hydrogenated natural phosphatidylserine, hydrogenated semisynthetic phosphatidylserine, synthetic distearoylphosphatidylserine, synthetic dipalmitoylphosphatidylserine and synthetic diarachidoylphosphatidylserine.

8. A process as claimed in claim 1 wherein said gas is perfluorobutane and said phosphatidylserine is a dialkanoylphosphatidyl-serine.

9. A process as claimed in claim 1 wherein the aqueous medium employed in step (i) further contains one or more additives selected from the group consisting of viscosity enhancers and solubility aids for the lipid material.

10. A process as claimed in claim 9 wherein said additive or additives are selected from the group consisting of alcohols and polyols.

11. A process as claimed in claim 1 wherein the lipid-stabilised dispersion formed in step (i) is washed prior to steps (ii) and (iii).

12. A process as claimed in claim 1 wherein the lipid-stabilised dispersion formed in step (i) is size fractionated prior to steps (ii) and (iii).

* * * * *